United States Patent [19]

Adachi et al.

[11] Patent Number: 4,833,246

[45] Date of Patent: May 23, 1989

[54] NOVEL PYRAZOLONE DYE

[75] Inventors: Keiichi Adachi; Shigeru Ohno; Yoshio Inagaki; Nobuo Seto; Yoshihiro Jinbo, all of Kanagawa, Japan

[73] Assignee: Fuji Photo Film Co., Ltd., Kanagawa, Japan

[21] Appl. No.: 127,309

[22] Filed: Dec. 2, 1987

[30] Foreign Application Priority Data

Dec. 2, 1986 [JP] Japan .................. 61-287295

[51] Int. Cl.$^4$ .................. C07D 231/22; C07D 231/24
[52] U.S. Cl. .................. 544/82; 544/79; 544/357; 548/364; 430/522
[58] Field of Search .................. 544/74, 82, 357; 548/364

[56] References Cited

U.S. PATENT DOCUMENTS 4,218,432  8/1980  Watanabe et al. .................. 548/364

Primary Examiner—Robert W. Ramsuer
Attorney, Agent, or Firm—Sughrue, Mion, Zinn, Macpeak & Seas

[57] ABSTRACT

A novel pyrazolone dye represented by the following formula (I), which can be effectively used as a filter dye, an irradiation inhibiting dye, an antihalation dye or the like in a photographic light-sensitive material:

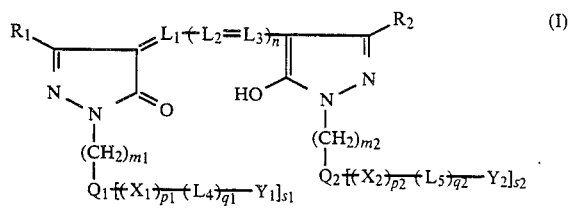

wherein $R_1$ and $R_2$ each represents —COOR or

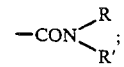

R and R' each represents a hydrogen atom, an alkyl group, or an aryl group or may combine with each other to form a 5- or 6-membered ring; $Q_1$ and $Q_2$ each represents an aryl group; $X_1$ and $X_2$ each represents a linkage group; $Y_1$ and $Y_2$ each represents a sulfo group or a carboxyl group; $L_1$, $L_2$ and $L_3$ each represents a methine group; $L_4$ and $L_5$ each represents an alkylene group; $m_1$ and $m_2$ each represents 1 or 2; n represents 0, 1 or 2; $p_1$ and $p_2$ each represents 0 or 1; $q_1$ and $q_2$ each represent 0, 1, 2, 3 or 4; and $s_1$ and $s_2$ each represents 1 or 2.

1 Claim, No Drawings

NOVEL PYRAZOLONE DYE

FIELD OF THE INVENTION

The present invention relates to a novel pyrazolone oxonol dye.

BACKGROUND OF THE INVENTION

Oxonol dyes are widely used in the photographic arts. These dyes are utilized as irradiation inhibiting dye, antihalation dye, filter dye, or so on in a silver halide photographic material.

The oxonol dyes are disclosed in British Pat. Nos. 1,177,429, 1,311,884, 1,338,799, 1,373,026 and 1,433,102, U.S. Patents 3,865,817, 3,867,149 and 4,266,014, Japanese Patent (OPI) Nos. 143342/83, 111641/84 and 168438/84 ("OPI" herein used means unexamined Japanese published application).

SUMMARY OF THE INVENTION

An object of the present invention is to provide a novel pyrazolone oxonol dye.

The above-described object is attained with a novel pyrazolone dye represented by formula (I):

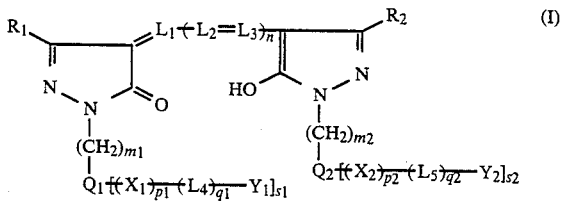

(which may be substituted), or an aryl group (which may be substituted) or may combine with each other to form a 5- or 6-membered saturated ring; $Q_1$ and $Q_2$ each represents an aryl group; $X_1$ and $X_2$ each represents a linkage group; $Y_1$ and $Y_2$ each represents a sulfo group or a carboxyl group; $L_1$, $L_2$ and $L_3$ each represents a methine group (which may be substituted); $L_4$ and $L_5$ each represents an alkylene group; $m_1$ and $m_2$ each represents 1 or 2; n represents 0, 1 or 2; $p_1$ and $p_2$ each represents 0 or 1; $q_1$ and $q_2$ each represents 0, 1, 2, 3 or 4; and $s_1$ and $s_2$ each represents 1 or 2.

DETAILED DESCRIPTION OF THE INVENTION

Of the compounds represented by the foregoing formula (I), those described below are preferred over others.

Preferred examples of groups represented by R and R' each include a hydrogen atom, an unsubstituted alkyl group containing not more than 5 carbon atoms (e.g., methyl, ethyl, propyl, isopropyl, butyl, pentyl, etc.), a substituted alkyl group (which contains as a substituent group, for instance, a carboxyl group, a sulfo group, a cyano group, a halogen atom (e.g., fluorine, chlorine, bromine, etc.), a hydroxyl group, or an alkoxy group containing not more than 4 carbon atoms), a phenyl group, and a substituted phenyl group (which contains as a substituent group, for instance, a carboxyl group, a sulfo group, a cyano group, a halogen atom (e.g., fluorine, chlorine, bromine, etc.), a hydroxy group, an alkyl group containing not more than 4 carbon atoms, an alkoxy group containing not more than 4 carbon atoms, an acyl group (e.g., acetyl), or a sulfonyl group (e.g., methanesulfonyl)).

Also, R and R' may combine with each other to form a 5- or 6-membered saturated ring which may contain carbon, nitrogen or oxygen as ring members and may be substituted or unsubstituted with substituents, such as the substituents that may be substituted on the substituted alkyl groups represented by R and R' (e.g., a pyrrolidine ring, a piperazine ring, or a morpholine ring).

Examples of groups represented by $Q_1$ and $Q_2$ each include a phenyl group, a naphthyl group and a substituted phenyl group (which contains as a substituent group, e.g., a halogen atom (e.g., fluorine, chlorine or bromine), an alkyl group (e.g., methyl or ethyl) or an alkoxy group (e.g., methoxy or ethoxy)).

Examples of groups represented by $L_1$, $L_2$ and $L_3$ each include an unsubstituted methine group and a substituted methine group (which contains as a substituent group an alkyl group (e.g., methyl or ethyl) or a phenyl group).

Examples of linkage groups represented by $X_1$ and $X_2$ each include

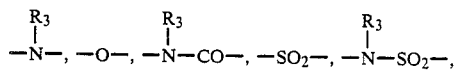

or a direct bond (wherein $R_3$ represents a hydrogen atom, an unsubstituted alkyl group containing not more than 5 carbon atoms (e.g., methyl, ethyl, butyl, etc.) or an alkyl group containing not more than 5 carbon atoms substituted with, e.g., an alkoxy group (e.g., methoxyethyl, etc.), a halogen atom (e.g., chloroethyl, etc.), a sulfo group (e.g., sulfoethyl, sulfobutyl, etc.), a carboxyl group (e.g., carboxymethyl, etc.), an alkoxycarbonyl group (e.g., methoxycarbonylethyl, etc.), a cyano group (e.g., cyanoethyl, etc.), a sulfonamido group (e.g., methanesulfonamidoethyl, etc.), a carbonamido group (e.g., acetylaminoethyl, etc.), a carbamoyl group (e.g., ethylaminocarbonylethyl, etc.), a sulfamoyl group (e.g., ethylaminosulfonylpropyl, etc.), and so on).

Examples of alkylene groups represented by $L_4$ and $L_5$ each include $-CH_2-$, $-CH_2CH_2-$,

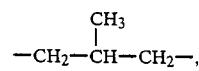

$-CH_2CH_2CH_2-$, $-(CH_2)_4-$, and the like.

When both $R_1$ and $R_2$ represent a carboxyl group in the foregoing formula (I), it is desirable that $p_1$, $p_2$, $q_1$ and $q_2$ are all zero. Further, both $Y_1$ and $Y_2$ are preferably sulfo group. When formula (I) is substituted in this manner, it is even more preferred that both $m_1$ and $m_2$ represent 1 and both $Q_1$ and $Q_2$ represent a phenyl group.

When $R_1$ and $R_2$ each represents

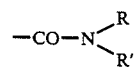

in the foregoing formula (I), it is desirable that R is a hydrogen atom, and R' is an alkyl group (including substituted ones), preferably an alkyl group containing not more than 4 carbon atoms. Further, it is preferred that $p_1$, $p_2$, $q_1$ and $q_2$ are all zero and boty $Y_1$ and $Y_2$ are desirably a sulfo group. When formula (I) is substituted in this manner, it is again even more desirable that both $m_1$ and $m_2$ are 1 and both $Q_1$ and $Q_2$ represent a phenyl group.

The compounds represented by formula (I) can be synthesized using various kinds of methods. As shown in the following reaction schemes, for example, they can be synthesized by condensing a pyrazolone of formula (II) and a compound represented by formula (IIIa), (IIIb), (IIIc), (IIId) or (IIIe), shown below, in the presence of a base.

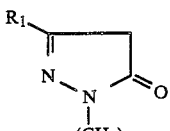

(II)

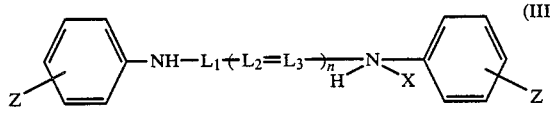

(IIIa)

HC(OC$_2$H$_5$)$_3$ (IIIb)

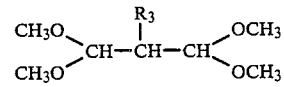 (IIIc)

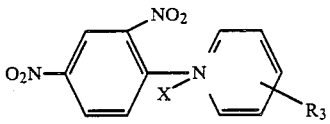 (IIId)

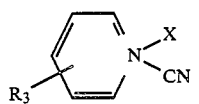 (IIIe)

In the foregoing formulae, $R_1$, $Q_1$, $X_1$, $Y_1$, $L_1$, $L_2$, $L_3$, $L_4$, $m_1$, $n$, $p_1$, $q_1$ and $s_1$ have the same meanings as in formula (I), respectively; Z represents a hydrogen atom, a nitro group, or a halogen atom (e.g., chlorine or bromine); $R_3$ represents an alkyl group (e.g., methyl, ethyl, etc.), or a phenyl group; and X represents an anion (e.g., chloride, bromide, iodide, perchlorate, methylsulfate, ethylsulfate, p-toluenesulfonate, etc.).

The novel pyrazolone nuclei-containing oxonol dyes of the present invention are effective as dyes for photographic light-sensitive materials, that is, as a filter dye, an irradiation inhibiting dye, an antihalation dye, and so on.

Specific examples of the compound of the present invention are illustrated below. However, the invention should not be construed as being limited to these examples.

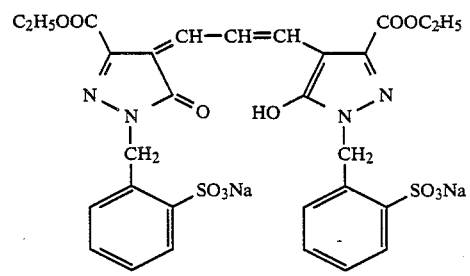

-continued
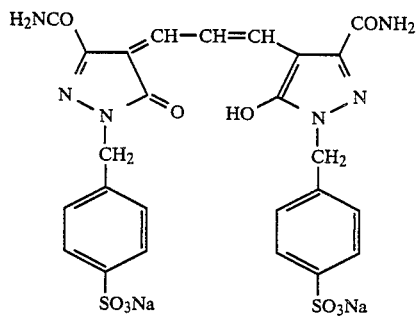  4
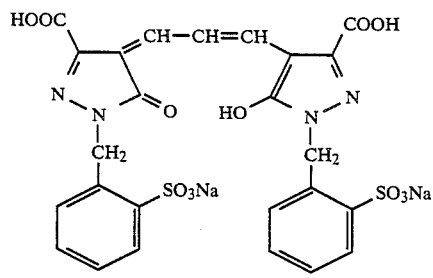  5
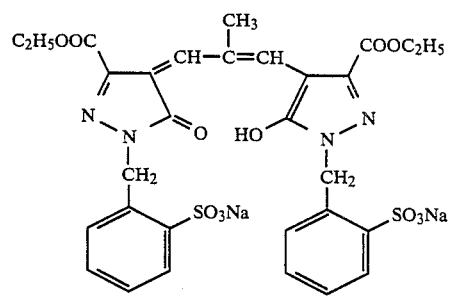  6
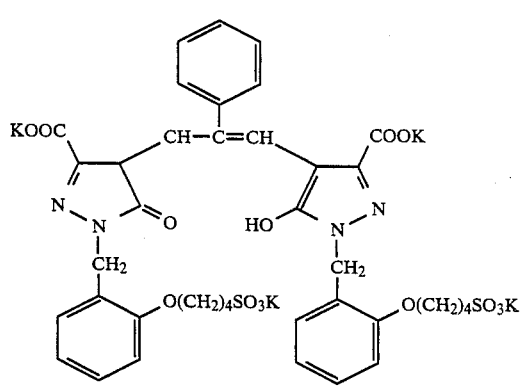  7
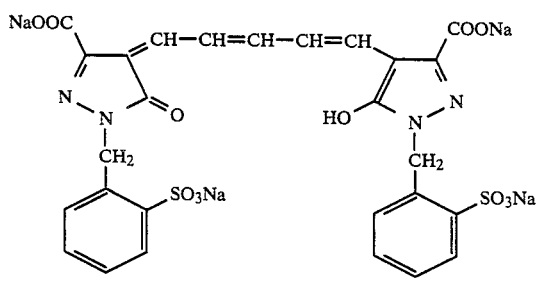  8

-continued
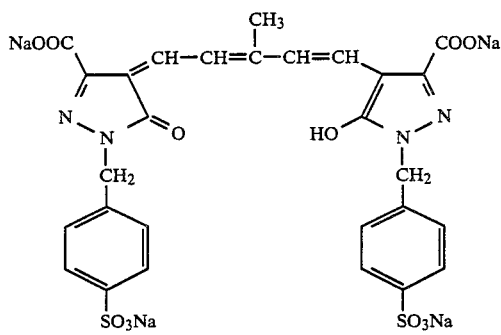
9
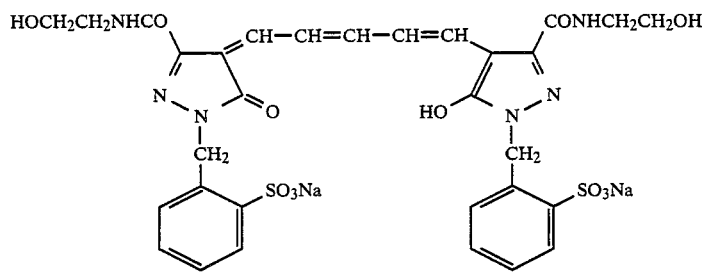
10
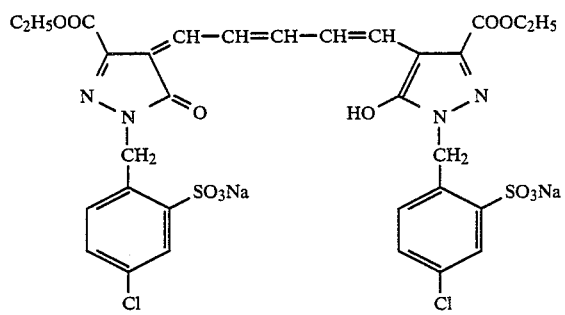
11
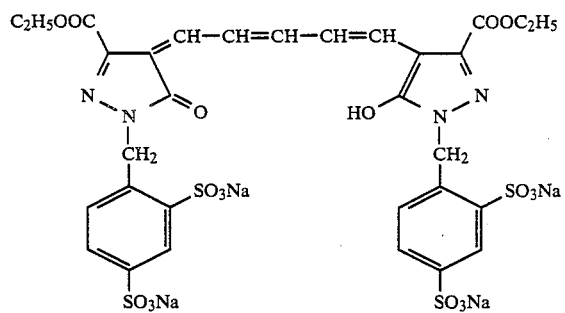
12
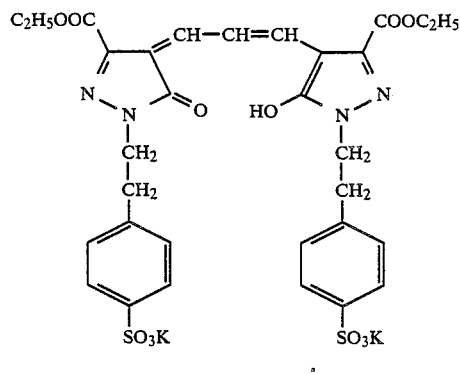
13

-continued
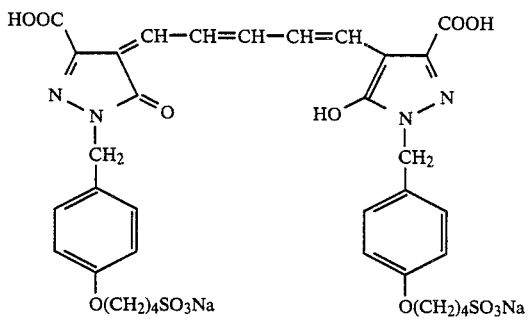
14
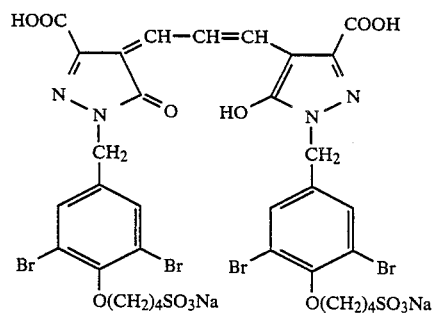
15
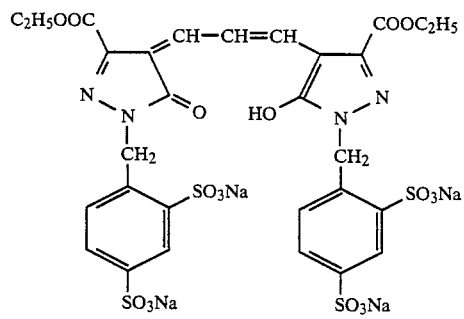
16
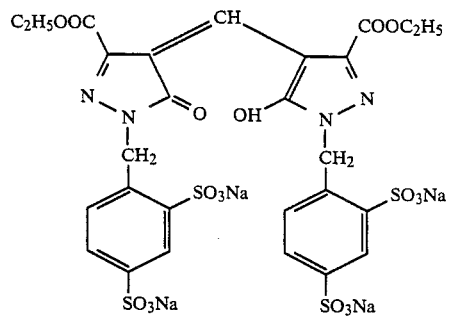
17
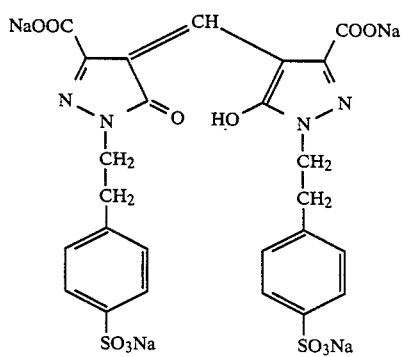
18

-continued
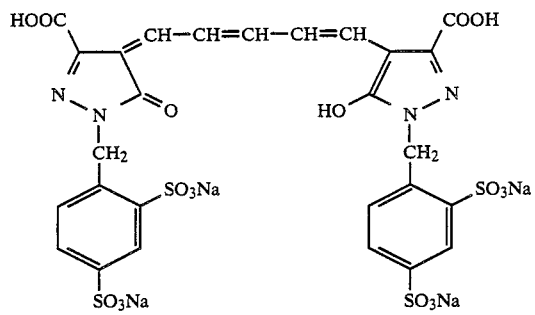 19
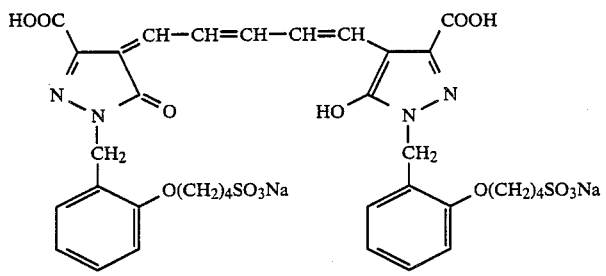 20
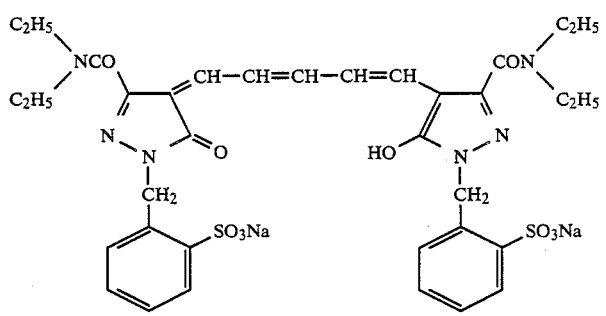 21
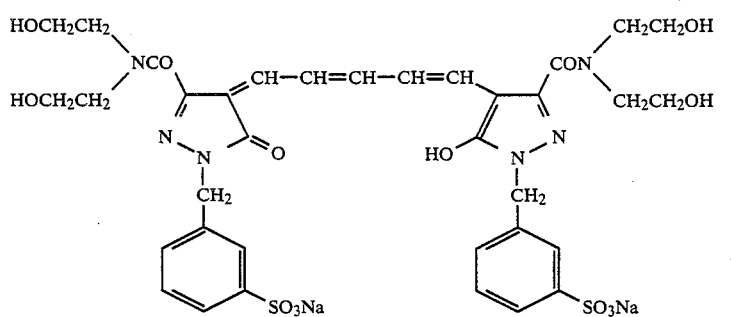 22
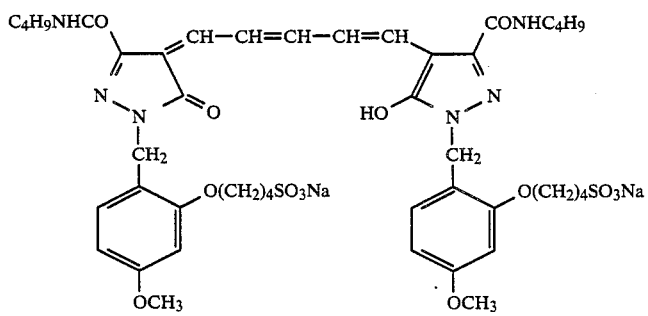 23

24
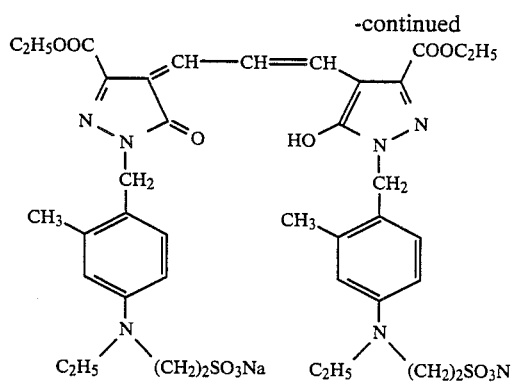
25
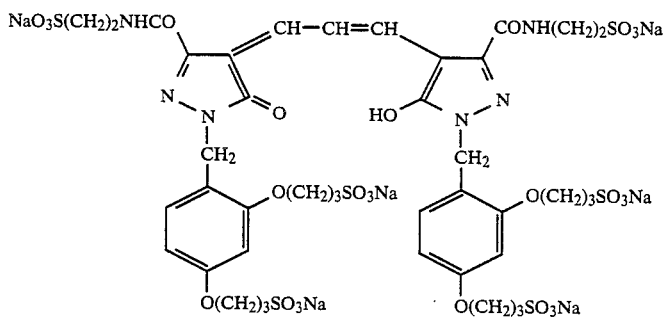
26
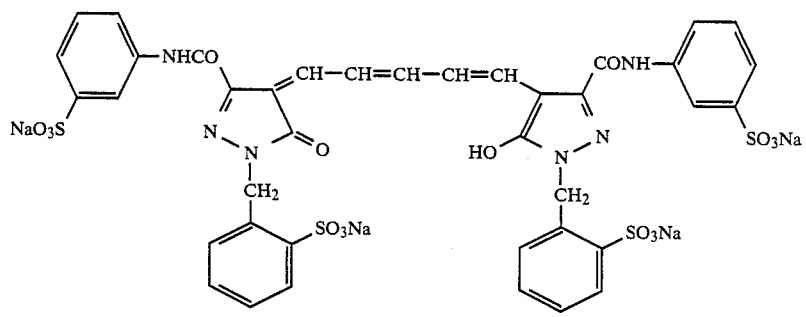
27
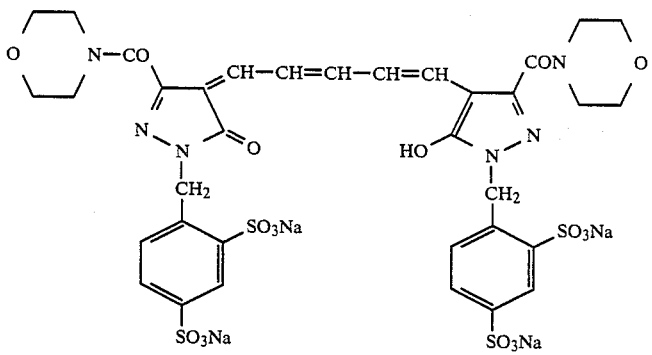
28
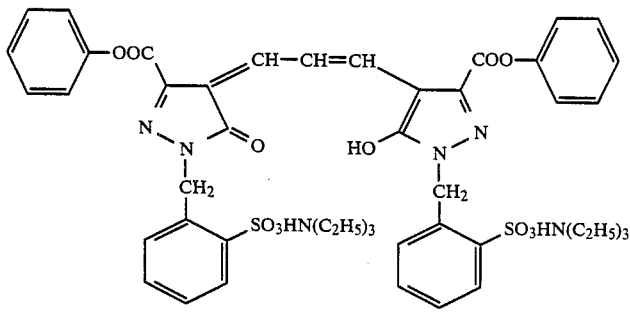

-continued
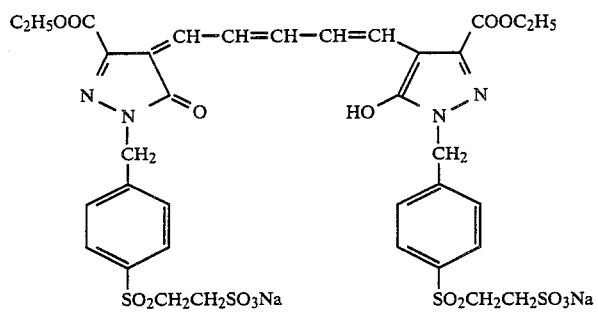
29
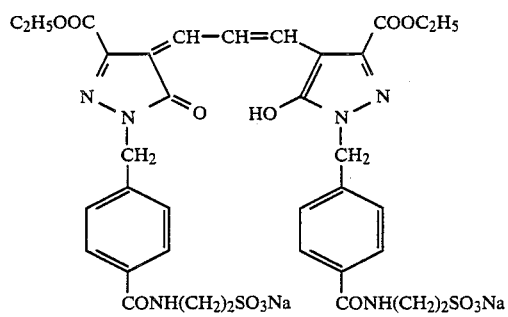
30
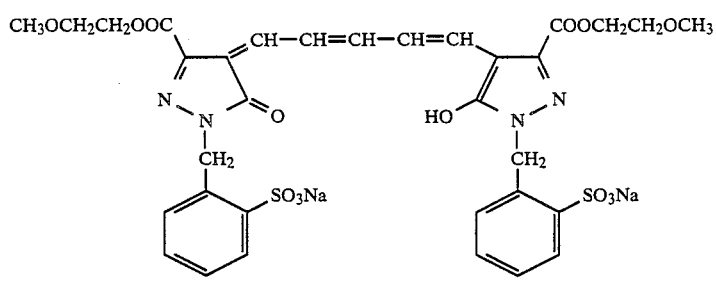
31
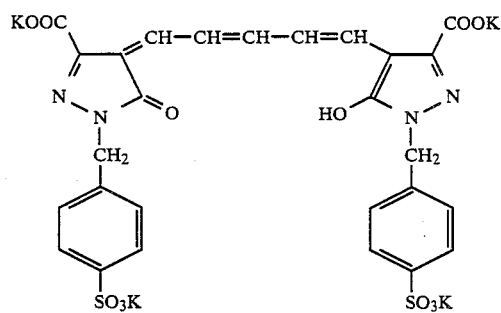
32
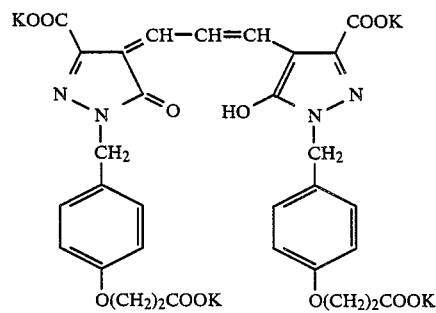
33

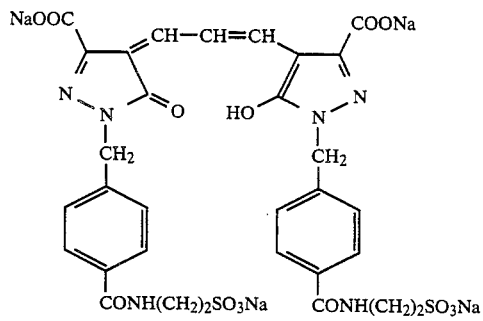
34
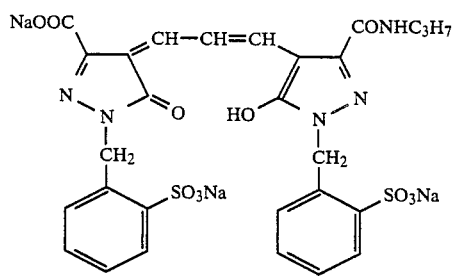
35
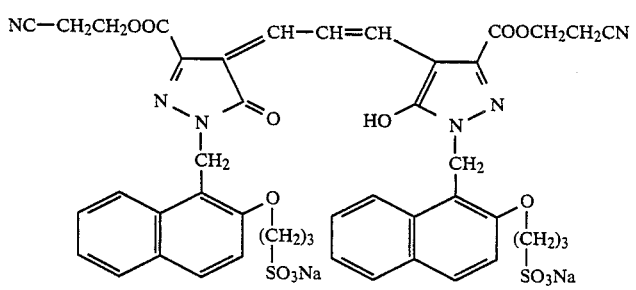
36
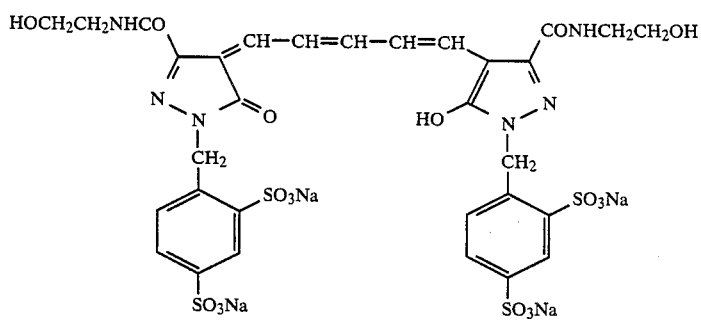
37
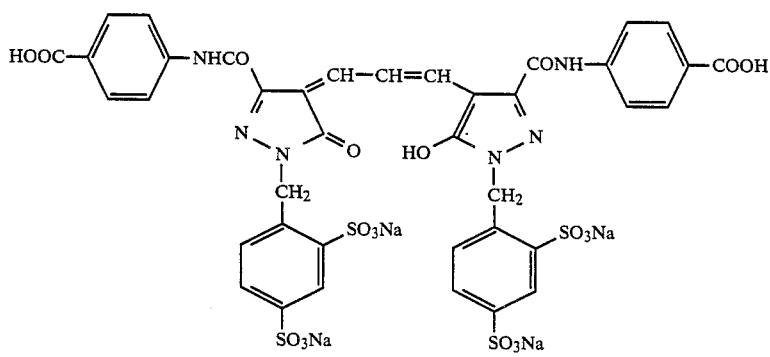
38

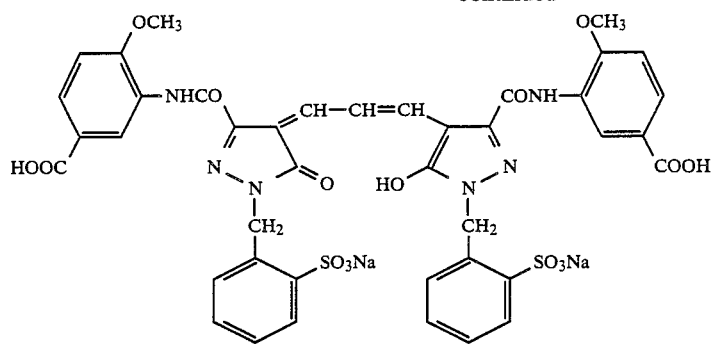
39
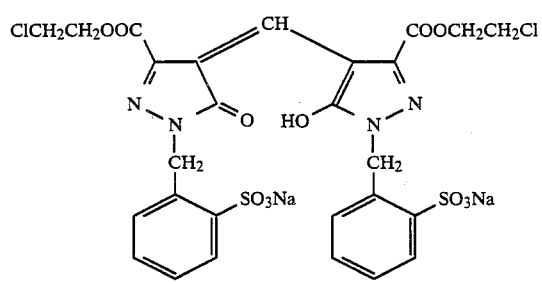
40
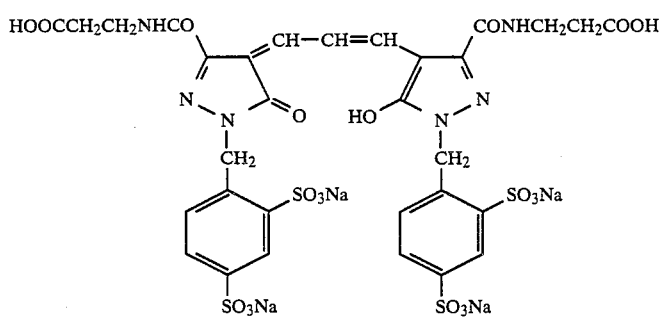
41
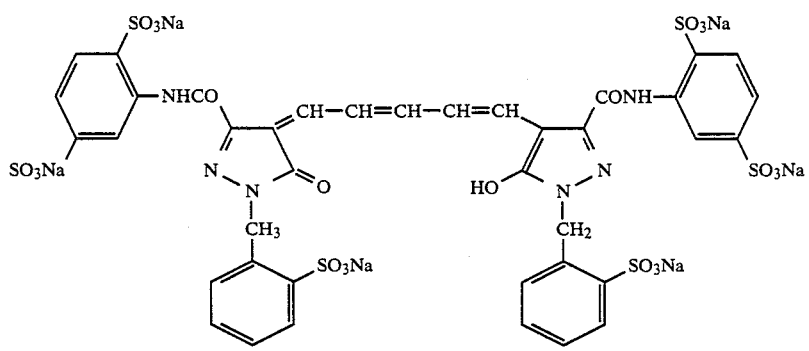
42
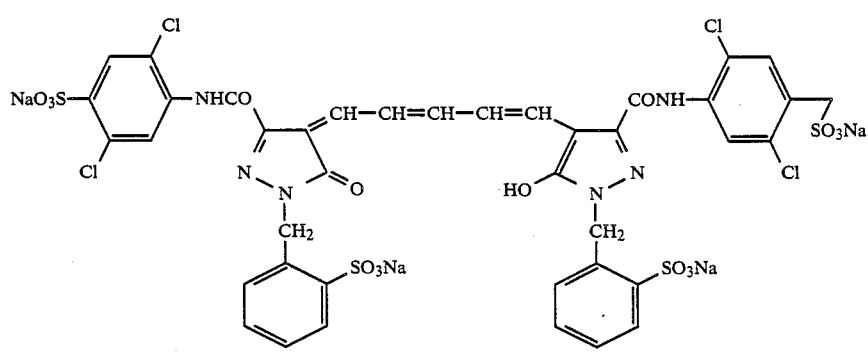
43

-continued
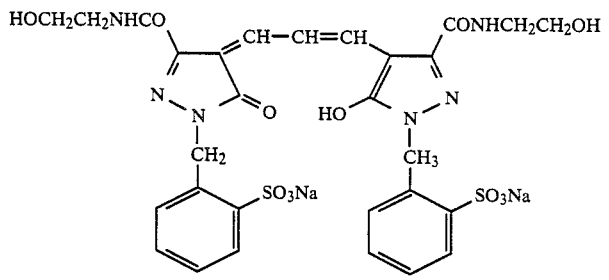 44
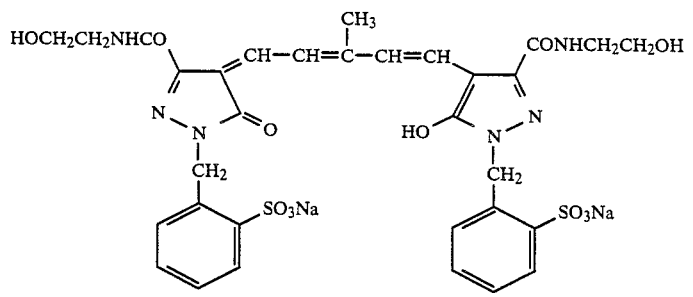 45
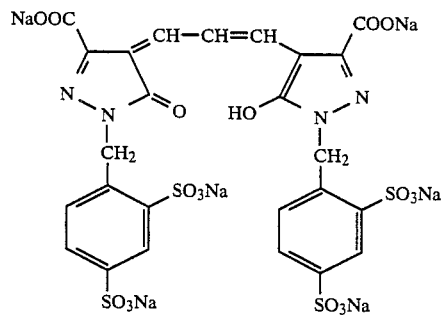 46
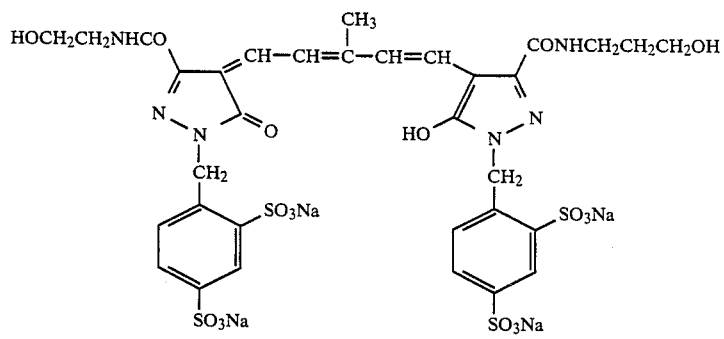 47
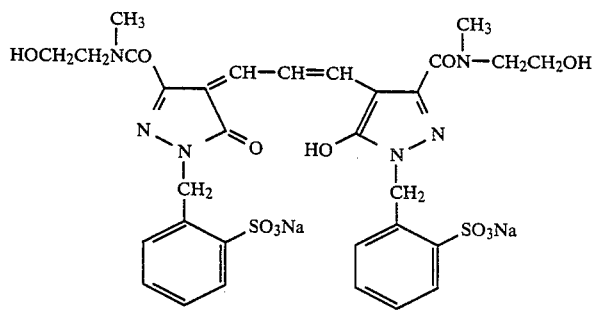 48

-continued

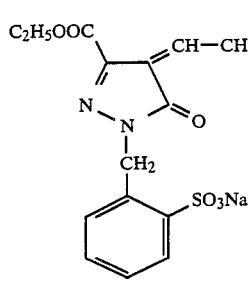 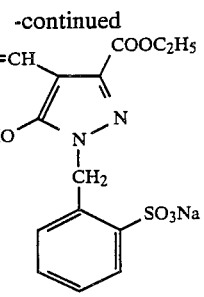

49

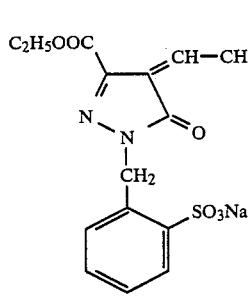 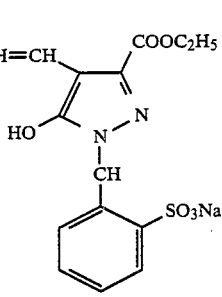

50

The dyes of the present invention are superior in some respects to conventional oxonol dyes. That is, when employed in a photographic system, though conventional oxonol dyes having an alkyl substituent at the 1-position of the pyrazolone ring have low stability and those having an aryl substituent at the 1-position of the pyrazolone ring tend to generate stains after photographic processing, the dyes of the present invention have the advantages that they are stable and hardly generate stains. Therefore, the dyes of the present invention can fulfil their function as a filter dye, an irradiation inhibiting dye, or an antihalation dye when added to an emulsion layer or other constituent layer of a photographic element.

Synthesis examples of specific compounds of the present invention are described in detail below. Unless otherwise specified herein, all parts, percents, ratios and the like are by weight.

SYNTHESIS EXAMPLE 1

Synthesis of Pyrazolone 1-(1) Synthesis of 3-Ethoxycarbonyl-1-(2-sulfobenzyl)-pyrazoline-5-one (Intermediate A)

A solution prepared by dissolving 104 g of sodium 2-formylbenzenesulfonate in 500 ml of methanol was added dropwise to 30 g of hydrazine hydrate with stirring under a cooled condition. Though the reaction temperature rose from 25° C., up to 35° C., the rise in reaction temperature ceased with time. Thereafter, the reaction mixture was allowed to stand overnight at room temperature. To the resulting reaction mixture was added 500 ml of isopropanol. Thereupon, white crystals precipitated. The crystals were filtered off, washed with 100 ml of isopropanol, and dried. Thus, 63 g of sodium 2-sulfobenzaldehydehydrazone (A-1) was obtained. Yield was 76 g and the melting point was above 300° C.

A 46 g portion of (A-1) obtained in the above-described manner was dissolved in 120 ml of ethanol and 60 ml of water, and then was placed in an autoclave having an inner volume of 500 ml. Further, 1 g of palladium/carbon catalyst was added to the foregoing solution, and a hydrogen pressure was adjusted to 40 kg/cm². Under this condition, the reaction was run at 30° C. for a period of 3 hours. After the reaction mixture was cooled to room temperature, the catalyst was filtered out and the solvent was distilled away therefrom under reduced pressure. Upon addition of 200 ml ethanol to the resulting reaction mixture, 2-sulfobenzylhydrazine (A-2) was obtained in the form of white crystals. Yield was 36 g and the melting point was above 300° C.

36 g of crude (A-2) was dispersed into 150 ml of acetic acid, and thereto was added an ethanol solution containing 36 g of sodium oxaloacetate diethyl ester to result in conversion into a nearly homogeneous solution. The heating of this reaction mixture was continued for 3 hours with stirring so as to keep the temperature of the reaction mixture at 90° C. After cooling to room temperature, 50 ml of hydrogen chloride dissolved in ethanol (obtained by bubbling hydrogen chloride gas into ethanol in a concentration of 36 wt%) was added to precipitate sodium chloride. After removal of sodium chloride by filtration, 500 ml of acetone was added to the filtrate to precipitate 42.3 g of Intermediate A. Yield was 78% and the melting point was 257° to 262° C.

1-(2) Synthesis of 3-Carboxy-1-(2-sulfobenzyl)pyrazoline-5-one (Intermediate B)

To a solution prepared by dissolving 7.8 g of sodium hydroxide in 20 ml of water was added 17.9 g of Intermediate A, and the resulting mixture was heated with stirring for 5 hours at a reaction mixture temperature of 70° C. After cooling the reaction mixture to room temperature, 16 ml of concentrated hydrochloric acid was added thereto, and the concentration treatment was continued under reduced pressure until a white crystalline precipitate started to separate from the reaction mixture, and then the concentrated solution was cooled with ice-cold water to precipitate the white crystals. These crystals were filtered off, washed with acetone, and dried. Thus, 14.2 g (yield: 87%) of Intermediate B was obtained. Melting Point: 223°–226° C.

1-(3) Synthesis of 3-(2-Hydroxyethylcarbamoyl)-1-(2-sulfobenzyl)pyrazoline-5-one (Intermediate C)

14.5 g of Intermediate A and 15.3 g of ethanolamine were mixed and made to react with each other over a period of 2 hours under a pressure reduced to 30 mm Hg inside the reaction container and a temperature kept at 120° C. outside the reaction container. After cooling to room temperature, the reaction product was dissolved in 30 ml of ethanol, and separated out in a crystallized condition upon addition of 300 ml of isopropanol. After filtration, the crystals were washed with isopropanol, and dried. Thus, 13 g (yield: 86.5%) of Intermediate C was obtained. Melting Point: 215°–219° C. (decomposed).

1-(4) Synthesis of 3-Ethoxycarbonyl-1-(2,4-disulfobenzyl)pyrazoline-one (Intermediate D)

Disodium 2,4-disulfobenzaldehydehydrazone (B-1) was prepared in the same manner as in Synthesis 1-(1), except disodium 2-formylbenzene-1,5-disulfonate was used in place of sodium 2-formylbenzenesulfonate. Further, disodium 2,4-disulfobenzaldehyde (B-2) was obtained through the same catalytic reduction as in Synthesis 1-(1), except (A-1) is replaced by (B-1). 90 g of crude (B-2) and 56 g of oxaloacetate diethyl ester (previously treated with the above-described hydrogen chloride dissolved in ethanol) were dissolved in 300 ml of ethanol, and heated under reflux for 1 hour. Methanol was concentrated to 150 ml and cooled to yield 99 g (yield: 80%) of Intermediate D. Melting Point: above 300° C.

1-(5) Synthesis of 3-Carboxy-1-(2,4-disulfobenzyl)-pyrazoline-5-one (Intermediate E)

Intermediate E was obtained in a yield of 85% according to the same process as in Synthesis 1-(2), except Intermediate E was used in place of Intermediate A. Melting Point: above 300° C.

1-(6) Synthesis of 3-Carboxy-1-(4-Sulfobenzyl)pyrazoline-5-one (Intermediate F)

3-Ethoxycarbonyl-1-phenylpyrazoline-5-one (F-1) was prepared in the same manner as in Synthesis 1-(1), except benzaldehyde was used in place of sodium 2-formylbenzenesulfonate. Further, (F-1) was hydrolyzed by the same method as used in Synthesis 1-(5) to be converted to 3-carboxy-1-phenylpyrazoline-5-one (F-2). 7 g of (F-2) was added to 28 ml of concentrated sulfuric acid and heated at 110° C. for 2 hours. After cooling, 140 ml of ethyl acetate was added to the reaction mixture and allowed to stand overnight to yield 7.8 g (yield: 82%) of Intermediate F. Melting Point: 276° C. (decomposed).

1-(7) Synthesis of 3-Ethoxycarbonyl-1-(4-sulfobutyloxybenzyl)pyrazoline-5-one (Intermediate G)

4-Hydroxybenzaldehyde was added to one equivalent of sodium hydroxide and then dissolved in methanol. Thereto was added 1.2 equivalents of butanesulfone. The resulting mixture was heated under reflux over a 30 hour period. Upon cooling, potassium 4-sulfobutyloxybenzaldehyde (G-1) to be used as a starting material was obtained. (G-1) underwent the same reaction procedure as employed in Synthesis 1-(2) to yield Intermediate G. Melting Point: 171°–173° C.

1-(8) Synthesis of Potassium Salt of 3-Carboxy-1-(4-sulfobutyloxybenzyl)pyrazoline-5-one (Intermediate H)

Intermediate G was converted to Intermediate H in the same manner as in Synthesis 1-(2), except the reaction was run using potassium hydroxide in place of sodium hydroxide. Melting Point: 118°–122° C.

SYNTHESIS EXAMPLE 2

Synthesis of Compound 3

To 50 ml of ethanol were added successively 5.2 g of Intermediate A, 4.2 ml of triethylamine, and 1.5 g malondialdehyde dianil hydrochloride. The mixture was heated under reflux for 3 hours to become a homogeneous solution. A solution prepared by dissolving 1.2 g of sodium acetate in 15 ml of methanol was added to this hot solution with stirring. Then 25 ml of isopropanol was further added thereto to precipitate dark violet crystals. These crystals were filtered off, washed with isopropanol, and dried. Thus, 2 g of Compound 3 was obtained. Melting Point: above 300° C., $\lambda_{max}^{H2O}$: 551 nm, $\epsilon 6.73 \times 10^4$.

SYNTHESIS EXAMPLE 3

Synthesis of Compound 5

4.8 g of Intermediate B, 50 ml of methanol and 6.3 ml of triethylamine were mixed, and thereto was added 1.5 g of malondialdehyde dianil hydrochloride. This mixture was subjected to the same treatments as in Example 2 yield 3 g of Compound 5. Melting Point: above 300° C., $\lambda_{max}^{H2O}$: 536 nm, $\epsilon 6.33 \times 10^4$.

SYNTHESIS EXAMPLE 4

Synthesis of Compound 8

7.4 g of Intermediate B, 50 ml of methanol and 7.5 ml of triethylamine were mixed, and cooled in an ice bath. Further, 2.8 g of glutaconaldehyde dianil hydrochloride was added thereto and stirred over a period of 3 hours. Then 50 ml of a methanol solution containing 4.2 g of sodium acetate was added to the reaction mixture, and therefrom dark violet crystals separated out upon addition of 25 ml of isopropanol. The crystals were filtered off, washed with isopropanol, and dried. Thus, 5.4 g of Compound 8 was obtained. Melting Point: above 300° C., $\lambda_{max}^{H2O}$: 626 nm, $\epsilon 7.89 \times 10^4$.

SYNTHESIS EXAMPLE 5

Synthesis of Compound 10

8 g of Intermediate C, 30 ml of methanol and 3.8 ml of triethylamine were mixed and cooled. Thereto 3 g of glutaraldehyde dianil salt and 2 ml of acetic anhydride were added successively. After 1 hour's reaction at room temperature, the reaction mixture precipitated black crystals by addition of 20 ml of isopropanol. The crystals were filtered off, washed with isopropanol and dried. Thus, 6.1 g of Compound 10 was obtained. Melting Point: above 300° C., $\lambda_{max}^{H2O}$: 633 nm, $\epsilon 8.8 \times 10^4$.

SYNTHESIS EXAMPLE 6

Synthesis of Compound 12

Compound 12 was obtained in the same manner as in Example 5, except Intermediate D was used in place of Intermediate B. Melting Point: above 300° C., $\lambda_{max}^{H2O}$: 640 nm, $\epsilon 7.02 \times 10^4$.

SYNTHESIS EXAMPLE 7

Synthesis of Compound 19

Compound 19 was obtained in the same manner as in Example 4, except Intermediate E was used in place of Intermediate B. Melting Point: above 300° C., $\lambda_{max}^{H2O}$: 627 nm, $\epsilon 6.82 \times 10^4$.

SYNTHESIS EXAMPLE 8

Synthesis of Compound 32

Compound 32 was obtained in the same manner as in Example 4, except Intermediate F was used in place of Intermediate B. Melting Point: above 300° C., $\lambda_{max}^{H2O}$: 627 nm, $\epsilon 6.30 \times 10^4$.

SYNTHESIS EXAMPLE 9

Synthesis of Compound 14

Compound 14 was obtained in the same manner as in Example 4, except Intermediate H was used in place of Intermediate B. Melting Point: 261° C. (decomposed), $\lambda_{max}^{H2O}$: 628 nm, $\epsilon 8.79 \times 10^4$.

SYNTHESIS EXAMPLE 10

Synthesis of Compound 20

3-Carboxy-1-(2-sulfobutyloxybenzyl)pyrazoline-5-one was synthesized using 2-hydroxybenzaldehyde as a starting material and according to the same processes as in Synthesis 1-(7) and Synthesis 1-(8). The thus synthesized intermediate underwent the same reaction as in Synthesis Example 9 to yield Compound 20. Melting Point: 264°–269° C. (decomposed), $\lambda_{max}^{H2O}$: 628 nm, $\epsilon 7.39 \times 10^4$.

SYNTHESIS EXAMPLE 11

Synthesis of Compound 18

3-Carboxy-1-(2-phenylethyl)pyrazoline-5-one was obtained using phenylacetoaldehyde and according to the same method as used in Synthesis 1-(6). 6 g of the thus obtained intermediate, 50 ml of methanol and 7 ml of triethylamine were mixed, and thereto was added 1.6 g of N,N'-diphenylformamidine hydrochloride. This mixture was heated for 2 hours to become a homogeneous solution. To this solution was added 50 ml of a methanol solution containing 4.5 g sodium acetate, and therefrom yellow crystals precipitated upon addition of 20 ml of isopropanol. The crystals were filtered off, washed with isopropanol and dried. Thus, Compound 18 was obtained in a yield of 4 g. Melting Point: above 300° C., $\lambda_{max}^{H2O}$: 452 nm, $\epsilon 2.10 \times 10^4$.

SYNTHESIS EXAMPLE 12

The following dyes were also synthesized in the same manner as described in Synthesis Example 11.

| | | | |
|---|---|---|---|
| 12-(1) | (Compound 1) | Yellow crystals | $\lambda_{max}^{H2O}$: 453 nm |
| 12-(2) | (Compound 2) | " | $\lambda_{max}^{H2O}$: 461 nm |
| 12-(3) | (Compound 4) | Dark violet crystals | $\lambda_{max}^{H2O}$: 544 nm |
| 12-(4) | (Compound 6) | " | $\lambda_{max}^{H2O}$: 556 nm |
| 12-(5) | (Compound 7) | " | $\lambda_{max}^{H2O}$: 553 nm |
| 12-(6) | (Compound 9) | " | $\lambda_{max}^{H2O}$: 633 nm |
| 12-(7) | (Compound 11) | " | $\lambda_{max}^{H2O}$: 641 nm |
| 12-(8) | (Compound 13) | " | $\lambda_{max}^{H2O}$: 545 nm |
| 12-(9) | (Compound 15) | " | $\lambda_{max}^{H2O}$: 534 nm |
| 12-(10) | (Compound 16) | " | $\lambda_{max}^{H2O}$: 551 nm |
| 12-(11) | (Compound 17) | Yellow crystals | $\lambda_{max}^{H2O}$: 460 nm |
| 12-(12) | (Compound 21) | Dark violet crystals | $\lambda_{max}^{H2O}$: 631 nm |
| 12-(13) | (Compound 22) | " | $\lambda_{max}^{H2O}$: 632 nm |
| 12-(14) | (Compound 23) | " | $\lambda_{max}^{H2O}$: 632 nm |
| 12-(15) | (Compound 24) | " | $\lambda_{max}^{H2O}$: 551 nm |
| 12-(16) | (Compound 25) | " | $\lambda_{max}^{H2O}$: 630 nm |
| 12-(17) | (Compound 26) | Dark violet crystals | $\lambda_{max}^{H2O}$: 633 nm |
| 12-(18) | (Compound 27) | " | $\lambda_{max}^{H2O}$: 632 nm |
| 12-(19) | (Compound 28) | " | $\lambda_{max}^{H2O}$: 553 nm |
| 12-(20) | (Compound 29) | " | $\lambda_{max}^{H2O}$: 641 nm |
| 12-(21) | (Compound 30) | " | $\lambda_{max}^{H2O}$: 551 nm |
| 12-(22) | (Compound 31) | " | $\lambda_{max}^{H2O}$: 638 nm |
| 12-(23) | (Compound 33) | " | $\lambda_{max}^{H2O}$: 534 nm |
| 12-(24) | (Compound 34) | " | $\lambda_{max}^{H2O}$: 537 nm |
| 12-(25) | (Compound 35) | " | $\lambda_{max}^{H2O}$: 539 nm |
| 12-(26) | (Compound 36) | " | $\lambda_{max}^{H2O}$: 550 nm |
| 12-(27) | (Compound 37) | " | $\lambda_{max}^{H2O}$: 633 nm |
| 12-(28) | (Compound 38) | " | $\lambda_{max}^{H2O}$: 545 nm |
| 12-(29) | (Compound 39) | " | $\lambda_{max}^{H2O}$: 544 nm |
| 12-(30) | (Compound 40) | Yellow crystals | $\lambda_{max}^{H2O}$: 465 nm |
| 12-(31) | (Compound 41) | Dark violet crystals | $\lambda_{max}^{H2O}$: 544 nm |
| 12-(32) | (Compound 42) | " | $\lambda_{max}^{H2O}$: 635 nm |
| 12-(33) | (Compound 43) | " | $\lambda_{max}^{H2O}$: 637 nm |
| 12-(34) | (Compound 44) | " | $\lambda_{max}^{H2O}$: 541 nm |
| 12-(35) | (Compound 45) | " | $\lambda_{max}^{H2O}$: 639 nm |
| 12-(36) | (Compound 46) | " | $\lambda_{max}^{H2O}$: 537 nm |
| 12-(37) | (Compound 47) | Dark violet crystals | $\lambda_{max}^{H2O}$: 639 nm |
| 12-(38) | (Compoune 48) | " | $\lambda_{max}^{H2O}$: 542 nm |
| 12-(39) | (Compound 49) | " | $\lambda_{max}^{H2O}$: 640 nm |
| 12-(40) | (Compound 50) | " | $\lambda_{max}^{H2O}$: 647 nm |

While the invention has been described in detail and with reference to specific embodiments thereof, it will be apparent to one skilled in the art that various changes and modifications can be made therein without departing from the spirit and scope thereof.

What is claimed is:

1. A pyrazolone dye represented by formula (I):

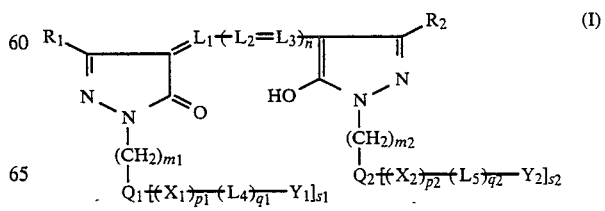

wherein $R_1$ and $R_2$ each represents -COOR or

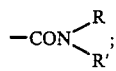

R and R' each represents a hydrogen atom, an alkyl group, or an aryl group or may combine with each other to form a 5- or 6-membered ring; $Q_1$ and $Q_2$ each represents an aryl group; $X_1$ and $X_2$ each represents a linkage group; $Y_1$ and $Y_2$ each represents a sulfo group or a carboxyl group; $L_1$, $L_2$ and $L_3$ each represents a methine group; $L_4$ and $L_5$ each represents an alkylene group; $m_1$ and $m_2$ each represents 1 or 2; n represents 0, 1 or 2; $p_1$ and $p_2$ each represents 0 or 1; $q_1$ and $q_2$ each represents 0, 1, 2, 3 or 4; and $s_1$ and $s_2$ each represents 1 or 2.

* * * * *